United States Patent
Grawe et al.

(10) Patent No.: US 9,211,485 B2
(45) Date of Patent: Dec. 15, 2015

(54) METHOD FOR PRODUCING CRYSTALLINE ACTIVE INGREDIENT PARTICLES

(75) Inventors: Detlef Grawe, Kleinromstedt (DE); Sabine Gliesing, Jena (DE)

(73) Assignee: Jesalis Pharma GmbH, Jena (DE)

( * ) Notice: Subject to any disclaimer, the term of this patent is extended or adjusted under 35 U.S.C. 154(b) by 0 days.

(21) Appl. No.: 13/640,025

(22) PCT Filed: Mar. 30, 2011

(86) PCT No.: PCT/EP2011/054956
§ 371 (c)(1),
(2), (4) Date: Oct. 8, 2012

(87) PCT Pub. No.: WO2011/124515
PCT Pub. Date: Oct. 13, 2011

(65) Prior Publication Data
US 2013/0040141 A1    Feb. 14, 2013

(30) Foreign Application Priority Data
Apr. 8, 2010   (DE) .......................... 10 2010 003 711

(51) Int. Cl.
*A61K 9/16*     (2006.01)
*B01D 9/00*     (2006.01)

(52) U.S. Cl.
CPC ............ *B01D 9/0013* (2013.01); *B01D 9/0036* (2013.01); *B01D 9/0054* (2013.01); *B01D 9/0081* (2013.01); *A61K 9/1688* (2013.01); *Y10T 428/2982* (2013.01)

(58) Field of Classification Search
CPC ........ B01D 9/00; B01D 9/0036; A61K 31/00; A61K 2800/412
USPC ......................... 427/212; 241/16, 38; 428/402
See application file for complete search history.

(56) References Cited

U.S. PATENT DOCUMENTS 3,510,266 A * 5/1970 Midler, Jr. ..................... 422/128
4,196,188 A    4/1980 Besins
(Continued)

FOREIGN PATENT DOCUMENTS

DE           26 59 251 A1    5/1978
DE     10 2005 053 862 A1    5/2007
(Continued)

OTHER PUBLICATIONS

Kamahara, T., et al., "Generation of Fine Pharmaceutical Particles via Controlled Secondary Nucleation under High Shear Environment during Crystallization—Process Development and Scale-up," *Organic Process Research & Development*, vol. 11, No. 4, pp. 699-703 (2007).

*Primary Examiner* — Erma Cameron
(74) *Attorney, Agent, or Firm* — Patterson Thuente Pedersen, P.A.

(57) ABSTRACT

A method and device for producing crystalline active ingredient particles. The active ingredient is crystallized from a supersaturated solution on the surface of particles of the active ingredient. A suspension of active ingredient particles is subjected to wet grinding in a supersaturated solution of the active ingredient in a first module. At least a part of the suspension is fed from the first module into the second module where it is cooled and simultaneously subjected to ultrasound. The suspension is fed back into the first module after cooling and being subjected to ultrasound. Active ingredient solution and optionally antisolvent are added to the suspension and active ingredient particles and liquid phase are extracted. A relative supersaturation of the active ingredient in the liquid phase of the suspension, relative to the entire liquid phase, is ≤90%, and the extracted active ingredient particles comprise a mean particle size of 10-500 μm.

7 Claims, 3 Drawing Sheets

(56) References Cited

U.S. PATENT DOCUMENTS

| | | | |
|---|---|---|---|
| 5,145,684 A | 9/1992 | Liversidge et al. | |
| 2003/0096013 A1* | 5/2003 | Werling et al. | 424/489 |
| 2003/0215516 A1* | 11/2003 | Grawe et al. | 424/489 |
| 2003/0215517 A1* | 11/2003 | Grawe et al. | 424/489 |
| 2003/0216360 A1 | 11/2003 | Grawe et al. | |
| 2005/0202095 A1 | 9/2005 | Daiziel et al. | |
| 2009/0297565 A1 | 12/2009 | Mëller et al. | |
| 2010/0072312 A1 | 3/2010 | Shiina et al. | |
| 2010/0184995 A1 | 7/2010 | Cohen et al. | |
| 2011/0065952 A1 | 3/2011 | Grawe et al. | |
| 2011/0144071 A1* | 6/2011 | Grawe et al. | 514/173 |
| 2011/0146678 A1* | 6/2011 | Ruecroft et al. | 128/203.15 |

FOREIGN PATENT DOCUMENTS

| | | |
|---|---|---|
| DE | 602 10 794 T2 | 5/2007 |
| DE | 10 2008 037 037 025 A1 | 2/2010 |
| EP | 0 499 299 A2 | 8/1992 |
| EP | 0 522 700 A2 | 1/1993 |
| EP | 1 497 308 B1 | 9/2006 |
| GB | 2 039 781 A | 8/1980 |
| WO | WO 03/033097 A2 | 4/2003 |
| WO | WO 03/091272 A1 | 11/2003 |
| WO | WO 2008/017331 A2 | 2/2008 |
| WO | 2009035558 * | 3/2009 |
| WO | WO 2009/035558 A1 | 3/2009 |
| WO | WO 2009/138055 A1 | 11/2009 |
| WO | WO2010007447 * | 1/2010 |

* cited by examiner

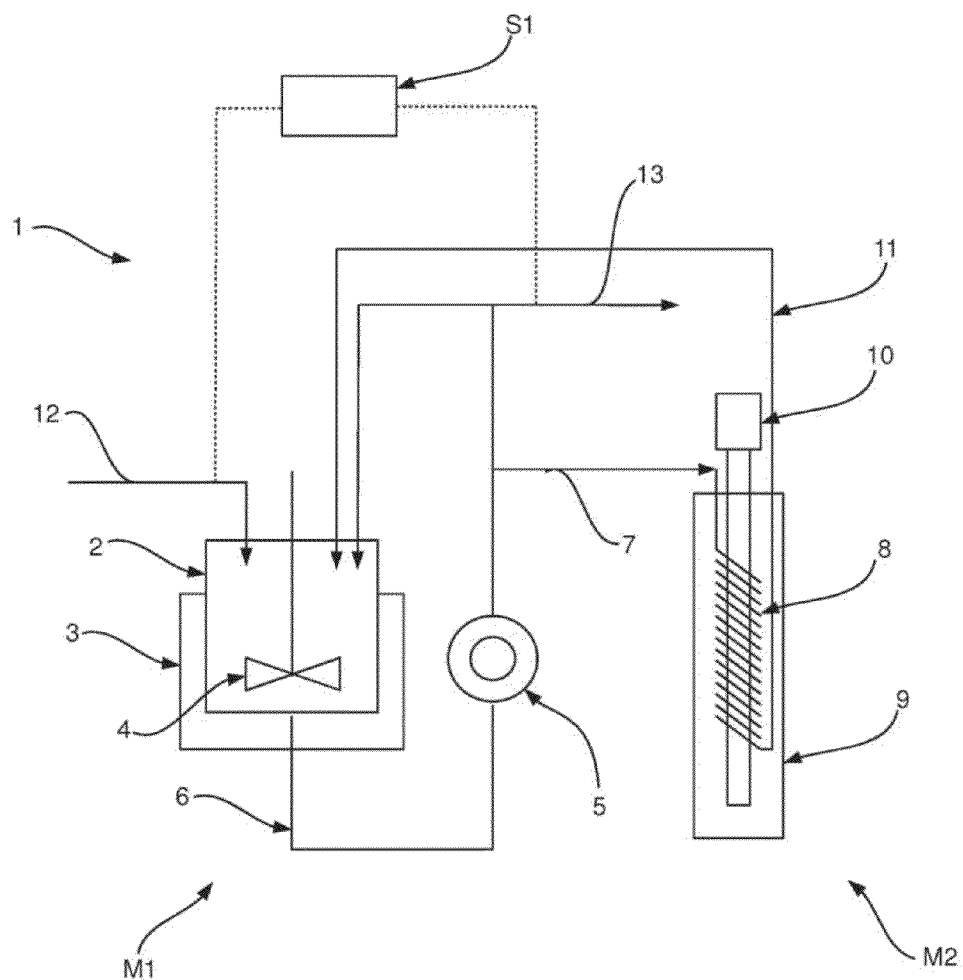

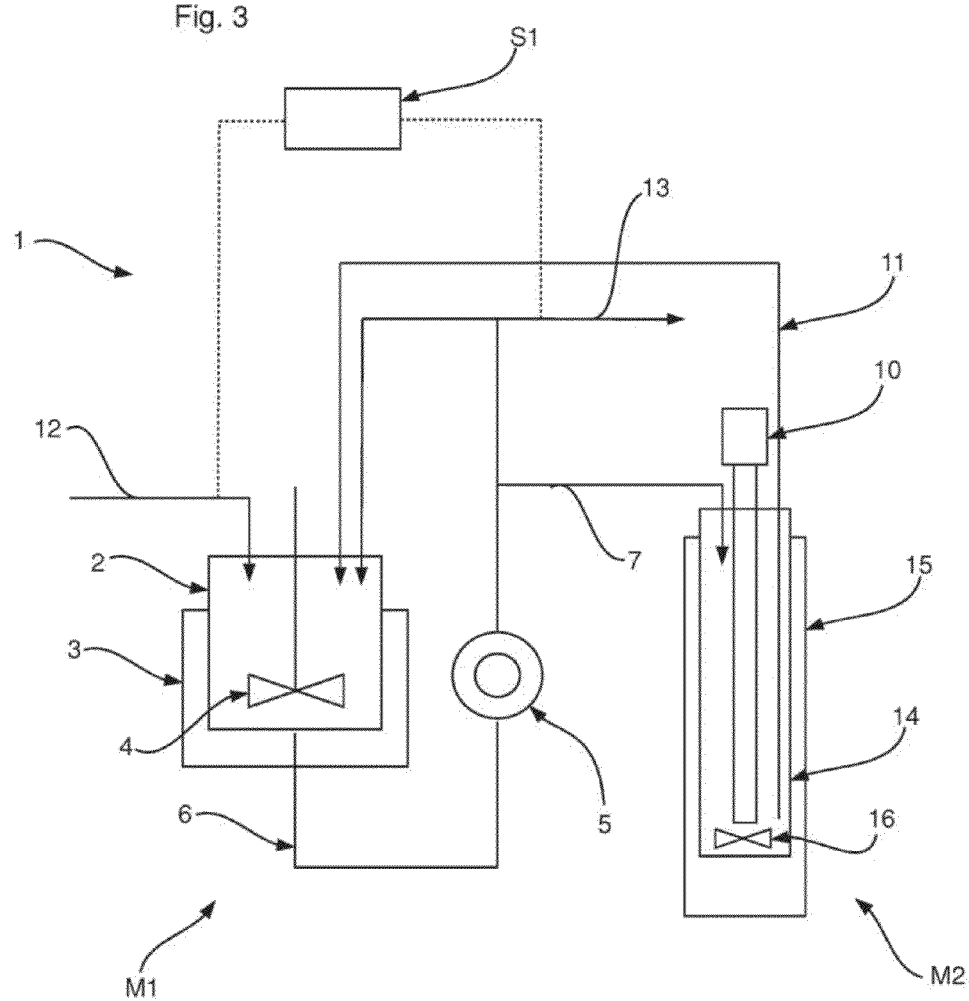

METHOD FOR PRODUCING CRYSTALLINE ACTIVE INGREDIENT PARTICLES

PRIORITY CLAIM

The present application is a National Phase entry of PCT Application No. PCT/EP2011/054956, filed Mar. 30, 2011, which claims priority from German Application Number 102010003711.7, filed Apr. 8, 2010, the disclosures of which are hereby incorporated by reference herein in their entirety.

TECHNICAL FIELD

The invention relates generally to a method for producing crystalline active ingredient particles, and more particularly a method wherein an active ingredient crystallizes from a slightly supersaturated suspension of the active ingredient accompanied by wet grinding, cooling and ultrasound treatment. Furthermore, the invention relates to the crystalline active ingredient particles obtainable according to this method and a device for carrying out the method.

BACKGROUND

Processing properties of active ingredient particles, for example their bulk density, wettability, pourability, stability, solubility properties etc., depend on the particle size and quite substantially on the particle size distribution. To achieve as rapid a release as possible from dosage forms, poorly soluble active ingredients are produced with as finely particulate a form as possible. On the other hand, in a retard form in which the release behavior is controlled via the particle size, generally a coarser grain size which controls the dissolution of the active ingredient particles within the desired time window is required.

To achieve good processing properties, the particle size distribution should be as narrowly limited as possible and be reproducibly generated. Also, for reasons of processability or stability of active ingredients, there is a need to produce active ingredients with a coarser, but defined and narrow, particle size distribution, wherein it is desirable that the particle size distribution is achieved directly by crystallization if at all possible without subsequent process steps such as sieving and grinding.

Grinding devices, such as, for example, rotor/stator devices, can be used for the production of fine-grained crystal particles and controlled influencing of the particle size of active ingredients.

In "Generation of fine Pharmaceutical Particles via Controlled Secondary Nucleation under High Shear Environment during Crystallization", Organic Process Research & Development 2007, 11, pp. 699-703, Kamahara et al. describe precipitation crystallization in a solvent-antisolvent system with the aim of achieving a strong secondary nucleation and thus as fine a grain size as possible (average particle size 8-10 µm) through high supersaturations in the shear zone of the dispersion unit. As the product suspension is circulated via crystallizer and rotor/stator, unsteady conditions with regard to concentration and supersaturation obtain if there is constant dosage of the active ingredient solution. With batch sizes of 3-20 kg, as are customary in the production of active ingredients, larger systems are generally required.

A rotor/stator grinding device in connection with a precipitation reaction for producing as fine-grained particles as possible is also described in WO 03/033097 A2. Solution and precipitant are continuously fed into the rotor/stator unit via separate feed lines and a high nucleation rate and thus a limitation of crystal growth is achieved in the shear zone of the dispersing unit.

The above-described methods are suitable for obtaining the finest possible grain sizes. However, the targeted production of coarser grain sizes in the range of average particle diameters of more than 10 µm, in particular of more than 20 µm is problematic with these precipitation reactions in the shear zone of the dispersant. Furthermore, bimodal grain sizes with high proportion of fine grains are produced by superimposing nucleation and grinding effects. In addition, the secondary nucleation rate and thus ultimately the grain size achieved depends on a large number of factors and thus harbors risks with regard to process monitoring and reproducibility.

A general problem during crystallization using wet-grinding devices, such as, e.g. rotor/stator systems, is the enormous input of dissipation heat, to which is generally added the heat of the hot active ingredient solution. As solubility is normally temperature-dependent, this heat must effectively be removed again from the system. This requires correspondingly large cooling surfaces. Due to the supersaturation naturally forming over these surfaces, these tend to become progressively encrusted (fouling). This leads to disruptions in the desired grain size by coarse particles of these crusts, blockages in the transport lines and a progressive deterioration of the heat transfer. The smaller the system, the more serious becomes the problem of heat removal and the fouling effects. A continuous operation in as small as possible and thus a low-cost system in which a stationary regime is to be maintained over an extended period of time for producing a defined grain size is not possible with these methods and systems.

In WO 03/091272 A1 it is described that, through subsequent treatment of a suspension of fine primary particles which has been obtained via crystallization with simultaneous wet grinding, a targeted and reproducible grain coarsening was able to be achieved by means of repeated partial dissolution and recrystallization through corresponding temperature profiles. Unlike the method of the above-mentioned WO 03/033097 A2, here the desired particle size distribution is not achieved predominantly by secondary nucleation, but by a better-controllable, gradual crystal growth process. However, it is disadvantageous that this is possible only via additional process steps and on an industrial scale, and only when operating in batches with correspondingly large and cost-intensive equipment. Furthermore, it is disadvantageous that crystal growth can be superimposed by the formation of agglomerates in the following tempering phase.

SUMMARY OF THE INVENTION

An objective of embodiments of the invention is to overcome the above-mentioned disadvantages of the prior art and to provide a crystallization method which produces a largely stable, narrow and low-agglomerate particle size distribution and can also deliver larger active ingredient quantities with high efficiency and at favorable cost. Furthermore, an object of the invention is to provide a device for carrying out the method.

In an embodiment, this objective is achieved by a method for producing crystalline active ingredient particles in which active ingredient crystallizes from a supersaturated solution on the surface of particles of the active ingredient, wherein in a first module, a suspension of active ingredient particles in a supersaturated solution of the active ingredient is subjected to wet grinding, at least part of the suspension of active ingredient particles is cooled in a second module and simultaneously exposed to ultrasound, the active ingredient particle suspension from the first module is fed into the second module, and the active ingredient particle suspension is returned to the first module after cooling and exposure to ultrasound, wherein active ingredient solution and optionally antisolvent are fed to the suspension and active ingredient particles as well as liquid phase are removed, wherein the relative supersaturation of the active ingredient in the liquid phase of the suspension, relative to the total liquid phase, is ≤90% and the removed active ingredient particles have an average particle size $d_{50}$ of 10-500 μm.

The method according to embodiments of the invention delivers, surprisingly largely independently of the physicochemical properties of the active ingredient, crystalline microparticles which have a very narrow particle size distribution and very few agglomerated particles, whereby outstanding processing properties of the obtained active ingredient particles are achieved.

Objectives of the invention are further achieved by a device for producing crystalline active ingredient particles with a first module which has a wet-grinding device in which active ingredient particles are wet-ground in a suspension, a second module which has a cooling device and an ultrasound source for simultaneously cooling and exposing the active ingredient suspension to ultrasound, a feed line with which active ingredient solution and optionally antisolvent can be fed to the first or second module, and a removal line with which active ingredient particles and liquid phase can be removed from the first or second module, wherein the first and second module are connected to each other such that at least part of the active ingredient particle suspension can be removed from the first module, guided through the second module and returned to the first module.

A "module" is understood, within the meaning of the invention, as a device, assembly, or arrangement. The term "active ingredient" is understood, within the meaning of the invention, as a pharmaceutical active ingredient, i.e. a substance which has a physiological effect if it is absorbed in sufficient quantity by the body of a living organism, in particular a mammal, and more particularly a human.

In a method according to an embodiment of the invention, a suspension of active ingredient particles is subjected to a wet grinding in a supersaturated solution of the active ingredient, whereby the particles are at least partially reduced. The production of the suspension at the start of the method can take place, for example, by adding product powder or via a starting crystallization. The particle size at the start of the method has barely any effect on the subsequent particle design.

The active ingredient crystallizes out from the suspension as a result of the supersaturation at the supplied crystal surfaces and the grinding of the active ingredient particles sets an upper limit to the particle sizes. Active ingredient solution, and optionally antisolvent, are fed to the suspension on the one hand and on the other hand active ingredient particles as well as liquid phase are removed. Feeding and removal are chosen depending on the rate of crystallization of the solvent, optionally fed antisolvent and the concentration of the supersaturated solution such that the supersaturation stays sufficiently low, in order that there is practically no nucleation and the crystallization occurs almost exclusively on the surface of the already present active ingredient particles.

To achieve a narrow particle size distribution, the decisive factor in the method according to embodiments of the invention is thus the supersaturation. A nucleation by correspondingly high supersaturations such as is sought in methods according to the prior art, in order to produce fine particles is expressly to be avoided here.

The supersaturation can be described by the relative supersaturation which is defined as follows:

$$\text{relative supersaturation} = (\text{concentration}_{active\ ingredient} - \text{solubility concentration}_{active\ ingredient})/\text{solubility concentration}_{active\ ingredient}$$

Concentration$_{active\ ingredient}$ is the concentration of the active ingredient in the liquid phase of the suspension, relative to the total liquid phase, in weight percent. The solubility concentration$_{active\ ingredient}$ is the concentration of the active ingredient in the liquid phase of the suspension at the saturation point relative to the total liquid phase in weight percent. The saturation point (solubility limit) represents the maximum soluble quantity in thermodynamic balance of the active ingredient in the liquid phase. For example, in a suspension which contains 30 wt.-% dissolved active ingredient in the liquid phase (supersaturated solution) and whose solubility concentration is 20 wt.-%, there is a relative supersaturation of 50%.

Above the solubility concentration (solubility limit), a metastable zone exists which extends up to the supersaturation limit above which nucleation then sets in for each substance in a specific solvent or solvent mixture and depending on the respective process conditions, e.g. stirring conditions, cooling rates etc. In one example, the concentration of the dissolved active ingredient remains inside the metastable zone in the liquid phase of the suspension.

In a method according to embodiments of the invention the relative supersaturation is ≤90% in the liquid phase of the suspension, relative to the total liquid phase. In this way the presence of the active ingredient particles, in particular of the freshly ground active ingredient particles with their fresh fracture edges, prevents or inhibits the formation in the solution of nuclei which would increase the portion of very small particles, whereby the particle size distribution would widen or become inhomogeneous. The relative supersaturation in the method according to embodiments of the invention in the liquid phase of the suspension, relative to the total liquid phase, is in the range of from 5-80%, and more particularly in the range of from 10-70%. Furthermore, it is preferred that the relative supersaturation is chosen such that it lies within the metastable zone. Furthermore, it is preferred that the relative supersaturation is chosen such that no nucleation occurs.

Suitable devices for wet grinding are dispersant apparatuses and homogenizers, and in particular rotor/stator grinding devices, such as, for example colloid mills, or else stirring or roll mills. In one example, rotor/stator apparatuses are used, as with these the proportion of the very small particles can be avoided very effectively by setting a defined gap width between rotor and stator.

Through exposure to ultrasound, agglomerations of the particles in the supersaturated solution are prevented or reduced and also the cooling surfaces are largely and continuously kept crust-free. In particular, as homogenous as possible a sound field should be emitted by the ultrasound equipment. The aim is to keep the cooling surface very largely free from crystallizing active ingredients. On the other hand, with direct exposure to ultrasound, the specific ultrasound output per surface must not be so high that it leads to a removal of sonotrode material and thus to a contamination of the product suspension. It was surprisingly found that both requirements are well met by ultrasound tube resonators as have hitherto been used only for cleaning baths. In one example, the power input lies in the range of from 50 to 500 W/L (watts per liter suspension). In one example, the drop in power output per surface unit of the ultrasound tube resonator lies in the range of from 0.5 to 5 W/cm$^2$.

Particles with an average particle size $d_{50}$ in the range of from 10 μm to 500 μm can be produced very reproducible with the method according to the invention. In one example, the average particle size $d_{50}$ is 15-300 μm, and more particularly 20-200 μm, and even more particularly 20-100 μm. The lower limit is primarily determined by the grinding effect alone which the wet-grinding device generates without the supply of feed. In some examples, $d_{10}$ comprises a value of 5-20 μm, and more particularly 8-18 μm.

The particle size and the particle size distribution (grain-size distribution) are determined with the help of a customary laser diffraction in a wet measurement which delivers a distribution curve of the particle sizes (Malvern System, Mastersizer E, wet measurement in the cuvette). $d_x$ means that x volume percent (vol.-%) of the particles have a diameter which is smaller than the given value. With a $d_{50}$ value of 1 μm 50 vol.-% of the particles thus have a diameter of less than 1 μm (micrometer). The $d_{50}$ value is a measure of the average (volume average) particle diameter and is therefore also called average particle diameter. With a $d_{10}$ of 15 μm and a $d_{90}$ of 50 μm 10 vol.-% of the particles have a diameter of less than 15 μm and 90 vol.-% of the particles have a diameter of less than 50 μm.

Sample preparation for wet measurement of the particle size and particle size distribution: 12.5 mg sample is dispersed in 25 ml aqueous surfactant solution (0.1% Tween 80 in water, saturated with active ingredient and filtered over a 0.2 μm filter) by means of ultrasound sonotrode (Hielscher, d=7 mm, 30% output) for 4 min. The thus-obtained suspension is added dropwise, accompanied by stirring, to the measuring vessel which contains filtered surfactant solution, until the obscuration (clouding) reaches 10% and the particle size distribution is determined by the above-described laser diffraction. An average value is determined from five measurements.

An advantage of the method according to embodiments of the invention is the generation of a very narrow particle size distribution. Additionally, largely agglomerate-free particles are obtained. This is achieved by the synchronous counterrotation of destructive grinding and ultrasound processes on the one hand and constructive crystal growth on the other hand. In the region of coarse grain sizes and agglomerates, above all the disintegration effect (grinding process and ultrasound) acts primarily in the direction of a reduction, and in the fine-grain region the crystal growth acts in the direction of an increase in the particle size. Thus, very narrow particle size distributions are achieved. The width of a particle size distribution (span) is defined as follows:

$$\text{span}=(d_{90}-d_{10})/d_{50}.$$

In examples, span values of ≤2.0, more particularly span values of ≤1.5 and even more particularly span values of ≤1.3 are achieved with the methods according to the invention.

The formation of agglomerates is very largely prevented or inhibited in the method according to embodiments of the invention above all by the ultrasound and in the coarse grain-size range also by the energy input of the wet-grinding device.

The degree of agglomeration of the crystallized active ingredient particles is described by the agglomeration factor (AGF). This is defined by the quotient of the diameter of the agglomerated particles and of the diameter of the non-agglomerated particles. This method is most informative for agglomeration when comparing the $d_{90}$ values. The agglomeration factor within the meaning of the present invention is therefore defined as follows:

$$\text{Agglomeration factor}=d_{90}(\text{agglomerated particles})/d_{90}(\text{non-agglomerated particles})$$

These two $d_{90}$ values are determined by different energy input into the sample to be tested.

With a high input of energy, existing agglomerates decompose and the following particle size measurement delivers the $d_{90}$ of the non-agglomerated particles. This $d_{90}$(non-agglomerated particles) is achieved according to the above-described sample preparation for wet measurement (using the Hielscher ultrasound sonotrode). Any agglomerates largely break down here into their primary particles.

With a low energy input on the other hand agglomerates are largely spared and the following particle size measurement delivers the $d_{90}$(agglomerated particles). For this 12.5 mg sample is dispersed in 25 ml aqueous surfactant solution (0.1% Tween 80 in water, saturated with active ingredient and filtered over 0.2 μm filters) for 30 seconds with an Ultra Turrax stirrer (d=8 mm, from Ika) at lowest speed (10000 rpm). The thus-obtained suspension is added dropwise accompanied by stirring to the measuring vessel which contains filtered surfactant solution, until the obscuration reaches 10% and the particle size distribution is determined by the above-described laser diffraction. An average value is determined from five measurements. The quotient d90(Ultra Turrax stirrer)/d90(ultrasound sonotrode) is a measure of the agglomeration factor. Values close to 1 indicate a low agglomeration.

Agglomeration factors of the particles of ≤1.6, more particularly ≤1.3, and even more particularly of 1.0 to 1.3 can be obtained with the method according to embodiments of the invention. With conventionally precipitated products, on the other hand, the agglomeration factors are generally between 2 and 3.

In one particular example, active ingredient particles with $d_{50}$=20-200 μm, $d_{10}$=8-18 μm, span≤1.3 and AGF≤1.3 are obtained by the method according to embodiments of the invention.

A further advantage of the method according to embodiments of the invention is the high crystallinity of the obtained product particles. By highly crystalline or crystalline particles is understood, within the meaning of the invention, particles which contain no or only small amorphous portions and are thus predominantly crystalline. In examples, the crystallinity, i.e. the crystalline portion, is 98 wt.-%. In one particularly example, the crystallinity of the active ingredient particles obtainable according to the method is 99.5 wt.-% and more particularly ≤99.9 wt.-%.

The crystallinity is determined by means of X-ray powder diffractometry (XRPD) (apparatus: Siemens D8, fixed sample position). After background correction the integral intensities in the X-ray diffractogram are compared with those of a reference material. This reference material can for example be a conventional precipitation product or a product according to a different production method with known crystallinity and granulation. Thus the crystallinity is a relative value which characterizes the degree of order compared with a reference sample. The relationship of the integral reflex intensities of particle sample and reference sample is therefore the quantitative expression of its difference in crystallinity.

The method according to embodiments of the invention can be carried out both discontinuously and also continuously. With a discontinuous operation the solution of the active ingredient and any antisolvents (non-solvents) is fed discontinuously, i.e. batchwise, and product particles are removed batchwise, in particular in the form of a suspension of product particles. In one example, a continuous procedure, in which a solution of the active ingredient and optionally antisolvent are added continuously and active ingredient particles as well as liquid phase, particularly in the form of a suspension of active ingredient particles, is continuously removed.

The suspension can be returned in the first module, for which for example pumps can be provided or the pumping action of the wet-grinding device, in particular of a rotor/stator grinding device, can be used. In one example, the ratio of the volumetric flow in the first module to the volumetric flow in the second module is then ≤10, and particularly 10 to 100.

With both the discontinuous and the continuous operation of the crystallization method according to embodiments of the invention, it is preferred that the volume of the crystalline suspension remains substantially constant, as a particularly uniform particle size distribution can thus be achieved. By "substantially constant" is understood in this context that the volume of the suspension fluctuates by not more than 20 vol.-%. In one example, the volume of the suspension, relative to the average value of the volume (100% value), is 90-110 vol.-%, in particular 95-105 vol.-%.

The solution of the active ingredient and thus also the suspension can comprise one or more solvents for the active ingredient. Suitable solvents are in particular alcohols, ketones and ethers, for example, methanol, ethanol, isopropanol, acetone and diethyl ether. In one example, water is used as antisolvent. By an antisolvent, it is understood, within the meaning of the invention, a liquid in which the active ingredient dissolves poorly. The solubility should be less than 0.5 g active ingredient per liter antisolvent. In one example, with the method according to an embodiment of the invention, the suspension consists of active ingredient particles and one or more solvents as well as optionally one or more antisolvents. In particular the suspension should not contain additional formed pieces.

In a particular embodiment of the method according to the invention for producing crystalline active ingredient particles, active ingredient is crystallized from a supersaturated solution on the surface of particles of the active ingredient, wherein in a first device a suspension of active ingredient particles is subjected to wet grinding, in particular with a rotor/stator grinding device, in a supersaturated solution of the active ingredient, part of the suspension is passed from the first device through a second device, cooled in the second device and simultaneously exposed to ultrasound, in particular with an ultrasound tube resonator, then the portion of the suspension is returned (recycled) to the first device, and active ingredient solution and optionally solvents are continually fed to the suspension and active ingredient suspension removed, with the result that there is a relative supersaturation of ≤90% of the active ingredient in the liquid phase of the suspension, relative to the total liquid phase, and the removed active ingredient particles have an average particle size $d_{50}$ of 10-500 µm. In this embodiment, the span of the removed active ingredient particles (product particles) is ≤2 and the agglomeration factor ≤1.6.

The crystalline active ingredient particles that can be obtained according to the method according to embodiments of the invention have an average particle size $d_{50}$ of 10-500 µm and a very narrow particle size distribution as well as a low agglomeration factor, in particular a span of ≤2.0 and an agglomeration factor of ≤1.6, wherein, as explained above, the span is defined as $(d_{90}-d_{10})/d_{50}$ and the agglomeration factor as $d_{90}$(agglomerated particles)/$d_{90}$(non-agglomerated particles).

Embodiments of the invention also relates to the use of the described crystalline active ingredient particles as medicinal products or in therapy. Furthermore, embodiments of the invention relates to a pharmaceutical composition comprising the crystalline active ingredient particles according to the invention.

The crystallization method according to embodiments of the invention can be carried out in a device that is relatively simple and low-cost, in terms of apparatus. The device according to an embodiment of the invention for producing crystalline active ingredient particles comprises a first module which has a wet-grinding device in which active ingredient particles are wet-ground in a suspension and a second module which has a cooling device and an ultrasound source for simultaneously cooling and exposing at least part of the active ingredient suspension to ultrasound.

The first module can be a vessel which is also called crystallizer below. The wet-grinding device is a rotor/stator grinding device, for example. The wet-grinding device can be located within the crystallizer, e.g. as Ultra Turrax stirring rod or arranged outside the crystallizer. Furthermore, the wet-grinding device can generate a circulation flow with the result that the first module is formed as circulating apparatus. In one particular embodiment, a colloid mill with adjustable gap width is used as rotor/stator apparatus. The particle size distribution of the suspension is seeking a target value which is determined mainly by the set gap width between the rotor and stator of the colloid mill and less by its rotational speed.

The device according to embodiments of the invention for producing crystalline active ingredient particles also comprises a feed, for example a fluid line, with which active ingredient solution and optionally antisolvent can be fed to the first or second module, and an offtake which likewise can be a fluid line, with which active ingredient particles and liquid phase can be removed from the first or second module. In one example, the feed and offtake are connected to the first module. The first and second modules are connected to each other, for example, by fluid lines, such that at least part of the active ingredient particle suspension can be removed from the first module, guided through the second module and returned to the first module. A pump can be provided for this, in particular in the fluid line between first and second modules.

In a particular embodiment, active ingredient solution (feed) can be supplied continuously to the crystallizer via the feed and product, i.e. active ingredient particle suspension, can be continuously removed via the offtake. The continuous supply of feed has the opposite influence on particle size as the grinding process. A supersaturation can be set by a temperature difference between feed and first module, in particular a crystallizer and by the feed rate such that a crystal growth takes place almost exclusively on the particles of the suspension. A dynamic balance with regard to particle size, thus a stationary operating point of the particle synthesis, then establishes itself between this crystal growth and the destruction by the grinding process or ultrasound. The supersaturation can be set also by admixing an antisolvent.

The level of the feed depends inter alia on the maximum rate of crystal growth in the so-called metastable zone between the solubility limit and the supersaturation limit without nucleation setting in. The surface-related rate of crystal growth (kg/m2*h), depending on the relative supersaturation and the width of the metastable zone, depending on the process conditions, behave in a material-specific way and can be determined experimentally by methods known to a person skilled in the art. The particle size distribution is thus controlled primarily by the gap width between rotor and stator, the feed and the removal of particles and liquid phase, such as, for example, in the form of an active ingredient particle suspension. Thus, unlike the very complex processes of primary and secondary nucleation in the methods of the prior art, this process can be better controlled and narrow particle size distributions can be produced in a targeted and reproducible manner.

The investigations within the framework of the present invention have shown that, even at maximum rotation speed and with the smallest possible gap, it is barely possible with rotor/stator grinding devices to grind a coarse-grained suspension to $d_{50}$ values of less than 10 µm. When using a rotor/stator grinding device as wet-grinding device the upper limit of the obtainable active ingredient particles of 500 µm is primarily determined by the maximum possible gap width of the rotor/stator unit, the disintegration effect of the ultrasound on larger particles and the crystal growth in the supersaturated solution.

In a particular embodiment, the device according to the invention also has a control module which controls the feed of the active ingredient solution and optionally antisolvent as well as the removal of the active ingredient particles and the liquid phase such that the relative supersaturation of the active ingredient in the liquid phase of the suspension, relative to the total liquid phase, is ≤90%. The control module can be designed as hardware and/or software or a conventional computer. Particularly, the control module controls the feed of the active ingredient solution and optionally antisolvent as well as the removal of the active ingredient particles and the liquid phase such that the relative supersaturation of the active ingredient in the liquid phase of the suspension, relative to the total liquid phase, is in the range of from 5-80%, and more particularly in the range of from 10-70%. In a embodiment active ingredient particles and liquid phase are removed in the form of an active ingredient particle suspension, i.e. removed from the device.

In a particular embodiment of the device according to the invention, the first and second modules are each circulating apparatuses and/or the ultrasound source is an ultrasound tube resonator. Furthermore, according to the embodiment, the combined capacity of first and second modules does not exceed 20 L (liters), in particular 10 L.

The cooling and exposure to ultrasound of the suspension in the second module, which can comprise a circulation cycle, can take place in different ways, as is described below in more detail by means of FIGS. 2 and 3.

It is understood that the features mentioned above and those still to be explained below can be used not only in the given combinations but also in other combinations or alone, without exceeding the scope of the present invention.

BRIEF DESCRIPTION OF THE DRAWINGS

Embodiments of the invention are explained in more detail below by way of example with the help of the attached Figures.

FIG. 2 is a schematic view of a device for producing crystalline active ingredient particles according to an embodiment of the invention.

FIG. 3 is a schematic view of a device for producing crystalline active ingredient particles according to another embodiment of the invention.

DETAILED DESCRIPTION OF THE FIGURES

Figure 1:
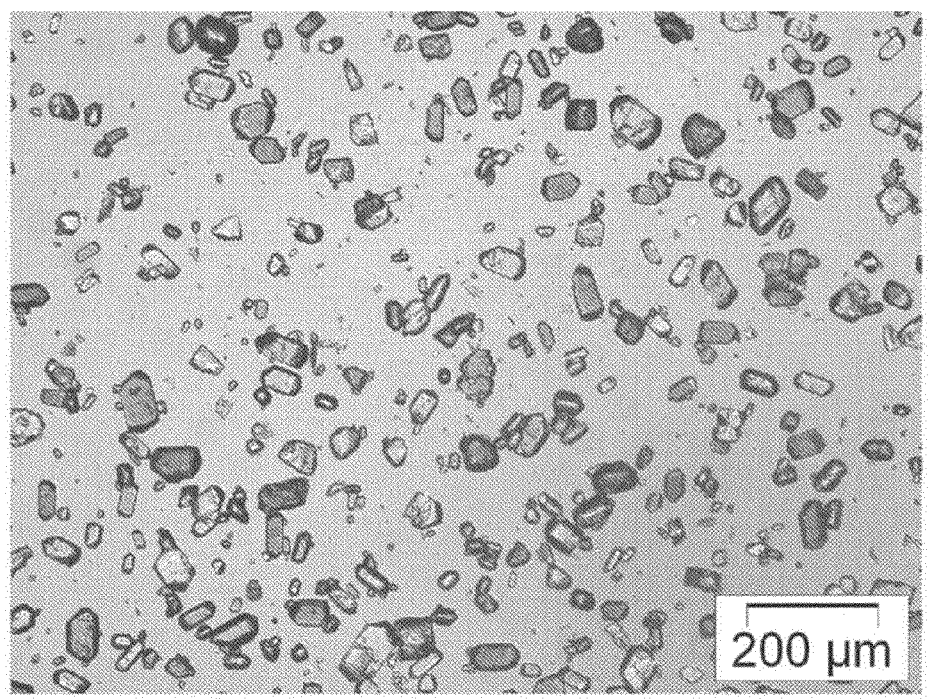
FIG. 1 shows a light-microscope image of the active ingredient particles according to an embodiment of the invention.

In the embodiment shown in FIG. 2, the device 1 according to the invention for producing crystalline active ingredient particles comprises a crystallizer 2 which is equipped with a heating device 3 and a stirrer 4, and a wet-grinding device 5, for example a rotor/stator grinding device. The wet-grinding device 5 is connected to the crystallizer 2 via fluid lines 6 and circulates the crystal suspension. Crystallizer 2, heating device 3, stirrer 4, wet-grinding device 5 and fluid lines 6 form the first module (M1) in this embodiment.

The embodiment shown further comprises a fluid line 7 via which crystal suspension is conveyed into a spiral coil 8, e.g. made of a glass tube or PTFE tube, which dips into a cooling device 9. The cooling device 9 is agitated with an ultrasound source 10. An ultrasound tube resonator is shown schematically here as ultrasound source 10 which exposes the bath as homogeneously as possible to ultrasound, e.g. at 20-25 KHz. The ultrasound oscillations are transmitted to the inside of the spiral coil 8. After cooling and exposure to ultrasound, the suspension is returned to the crystallizer 2 via the fluid line 11. Fluid line 7, spiral coil 8, cooling device 9, ultrasound source 10 and fluid line 11 form the second module (M2) in this embodiment.

Active ingredient solution is continuously fed into the crystallizer 2 via the feed line 12 and product in the form of an active ingredient suspension is removed via the removal line 13. The embodiment shown has a control module S1 which controls the feed of the active ingredient solution and optionally antisolvent as well as the removal of the active ingredient particles and the liquid phase such that the relative supersaturation of the active ingredient is ≤90% in the liquid phase of the suspension, relative to the total liquid phase. For this, the control module S1 can be connected to the feed 12 and the removal line 13 as illustrated in FIG. 2 with dotted lines. Valves and/or pumps can be controlled via the control module S1.

The exposure to ultrasound takes place indirectly in the embodiments shown in FIG. 2. A contamination of the suspension with sonotrode materials is thereby reduced or avoided altogether. The heat transfer with the coil principle is very effective and the hold-up of the system small. However, should coatings form in a few areas of the inside of the coil with longer processing times, these can be dissolved by periodic rinsing processes with a smaller amount of hot solvent.

The embodiment shown in FIG. 3 is a variation on the device according to FIG. 2. Identical reference numbers are given to identical system parts. Unlike in the device according to FIG. 2 the device does not comprise a spiral coil 8, but an agitator vessel 14 with jacket cooling 15 for direct exposure to ultrasound with the ultrasound source 10. The suspension is fed into the agitator vessel 14 close to the upper fill level. The suspension is stirred intensively near the bottom with a stirrer 16. The suspension, on the other hand, circulates slowly in the area of the ultrasound source 10. The ultrasound-impacted and cooled suspension is returned to the fluid line 11 near the bottom such that the fill level remains as constant as possible in the ultrasound-radiation vessel. The suspension is conveyed back into the crystallizer 2 via the line 11. Fluid line 7, ultrasound source 10, fluid line 11, agitator vessel 14, jacket cooling 15 and stirrer 16 form the second module (M2) in this embodiment.

In this embodiment, apart from the cooling surface all other system parts coming into contact with the system should have at least the same temperature as prevails in the crystallizer. Therefore, it is recommended, in order to avoid a complex tempering, to carry out the crystallization close to the ambient temperature. The temperature of the crystallizer wall itself should be controlled roughly around 2 to 8° C. above crystallization temperature in order to also avoid crusting in the longer term due to the higher supersaturation.

In order that when operating continuously, the stationary operating point of the process at which the particle size distribution no longer changes, is established as quickly as possible and the method can be better controlled, a particle should pass through the wet-grinding device and also the device for cooling and ultrasound agitation as often as possible before leaving the system in the product stream.

With a rotor/stator circuit outside the crystallizer, this can be achieved by setting the circulation flows such that the residence time of a particle in the crystallizer is as short as possible compared with the residence time in the overall system. Thus, the residence time in the crystallizer should be less than 5 minutes, better still less than one minute or particularly less than 20 sec. The circulation flow in the second module is advantageously chosen such that an adequate removal of heat is possible with as small as possible a temperature difference between the suspension temperature in the crystallizer and in the second module.

The feed and thus the product removal stream are such that the residence time of a particle in the overall system is sufficient to adequately reduce the supersaturation in the surrounding mother liquor. With many organic active ingredients this takes place within 10 to 60 min. Thus the feed and the product removal stream in the method according to the invention are smaller by a factor of 10 to 100 than the circulation flows. When using the apparatus according to FIG. 3, operation with a higher feed is naturally possible as the supersaturation is better reduced because of the larger system hold up compared with FIG. 2.

The suspension removed as product stream contains largely the particles formed by growth during crystallization. Oversize particles and agglomerates are largely prevented by the grinding and the ultrasound. Thus, in addition to an impairment of particle size, inclusions of mother liquors, which lead to purity and drying problems, are also prevented.

In order to prevent or inhibit a reagglomeration during a subsequent filtration and drying of the product particles, a solubility gradient can be generated in the rinsing medium when washing the filter cake. Operation starting with a rinsing medium close to the solubility in the mother liquors and finishing with a rinsing medium, wherein the active ingredient is virtually insoluble even at higher temperatures, is possible. "Higher temperatures" refers to any subsequent drying process above room temperature. The solubility gradient can be generated continuously or stepwise. A precipitation of active ingredient out of the mother liquor due to too rapid a reduction in solubility during the washing process must be avoided at all costs. The product is then dried using customary methods known to a person skilled in the art.

The following examples illustrate the invention.

EXAMPLE 1

In a system according to FIG. 2, 1000 g progesterone is placed in a crystallizer 2 and 4000 g acetone/water mixture with 33 wt.-% water in the double-walled vessel M2. Subsequently, a circulation is activated with a colloid mill (MK-Modul, MagicLab, IKA) at 16000 l/min and a throughput of approx. 400 l/h and the circulation cycle with pumps, each with approx. 60 l/h via the double-walled vessel M2. The double-walled vessel M2 is cooled to −20° C. in the jacket and crystallizer 2 heated to 28° C. in the jacket. The resonator is additionally cooled at the top by a cooling sleeve. 1000 g progesterone is added to the acetone/water mixture in vessel 2. The tube resonator which dips into the vessel M2 is powered with approx. 300 W. After 30 min circulation, a feed solution comprising an acetone/water mixture with 33% water and with 16 wt.-% progesterone is provided at 52° C. and pumped into the crystallizer 2 via a pump at 6 l/h. A temperature of 22-25° C. establishes itself in the crystallizer and a temperature of 17-20° C. in the vessel M2. At the same time as supplying the feed, product suspension is removed with the result that the fill levels of crystallizer 2 and the double-walled vessel M2 remain constant. The relative supersaturation in the crystallizer is 15% in the stationary regime.

The product suspension is sucked over a frit, washed with acetone/water mixture (33% water; 50% water) and air-dried. The particle size distribution, the agglomeration factor and the crystallinity of the dried product were determined as described above. The following parameters were determined:
$d10=12$ μm
$d50=34$ μm
$d90=64$ μm
span=1.5
AGF=1.3
crystallinity=100%
microscope image: see FIG. 1

Example 2

In a system according to FIG. 3, the external rotor/stator apparatus with a circulation cycle is replaced by an internal Ultra Turrax stirrer and the tube resonator by a conventional ultrasound ("US") bath. 500 g acetone/water mixture with 33 wt.-% water is placed in the crystallizer 2. 95 g progesterone is added accompanied by stirring to the acetone/water mixture in the crystallizer vessel 2. The Ultra Turrax (25G, Ika) is then activated in the crystallizer 2 at 14000 rpm and the circulation cycle with a pump, which pumps at 10 L/h suspension through a cooling coil of PTFE tube with an internal diameter of 3 mm and an overall length of 10 m which dips into the ultrasound-radiation vessel M2. An ultrasound bath filled with approx. 5 L, the temperature of which is controlled at approx. 5-10° C. with externally provided cold water, serves as ultrasound-radiation vessel. The US bath is then switched on. The temperature of crystallizer 2 is controlled at 28° C. in the jacket. After 30 min operation a feed solution comprising an acetone/water mixture with 33% water and with 16 wt.-% progesterone is provided at 52° C. and pumped into the crystallizer 2 at 1.2 l/h. A temperature of 24° C. to 26° C. establishes itself in the crystallizer 2. At the same time as supplying the feed, product suspension is removed, with the result that the fill level of crystallizer 2 remains constant. A suspension sample is removed from the product stream after 60 min. The relative supersaturation in the stationary regime is 23%.

The product suspension is sucked out via a fit, washed with acetone/water mixtures (33% water; 50% water) and air-dried. The particle size distribution, the agglomeration factor and the crystallinity of the dried product were determined as described above. The following parameters were determined:
$d10=10$ μm
$d50=26$ μm
$d90=45$ μm
span=1.3
AGF=1.1
crystallinity=100%

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention can comprise a combination of different individual features selected from different individual embodiments, as understood by persons of ordinary skill in the art.

The invention claimed is:

1. A method for producing crystalline active ingredient particles wherein active ingredient crystallizes from a supersaturated solution on the surface of particles of the active ingredient, the method comprising:
    subjecting, in a first module, a suspension of active ingredient particles in a supersaturated solution of the active ingredient to wet grinding;
    feeding at least part of the ground suspension of active ingredient particles in the supersaturated solution to a second module from the first module;
    cooling the at least part of the suspension of active ingredient particles in the second module and simultaneously exposing the at least part of the suspension to ultrasound; and
    returning the at least part of the active ingredient particle suspension to the first module after cooling and exposure to ultrasound, wherein at least a portion of the returned active ingredient particle suspension is subjected to wet grinding in the first module;
    wherein active ingredient solution and optionally antisolvent are fed to the suspension and active ingredient particles as in at least one of the first and second modules, and liquid phase of the suspension is removed from at least one of the first and second modules, and
    wherein a relative supersaturation of the active ingredient in the liquid phase of the suspension, relative to the total liquid phase, is ≤90% and removed active ingredient particles have an average particle size $d_{50}$ of 10-500 μm.

2. The method according to claim 1, wherein the relative supersaturation is 5-80%.

3. The method according to claim 1, wherein the relative supersaturation is chosen such that nucleation does not occur.

4. The method according to claim 1, wherein the wet grinding takes place with a rotor/stator grinding device.

5. The method according to claim 1, wherein a span of the removed active ingredient particles is ≤1.5, wherein the span is defined $(d_{90}-d_{10})/d_{50}$, and an agglomeration factor of the removed active ingredient particles is ≤1.3, wherein the agglomeration factor is defined as $d_{90}$(agglomerated particles)/$d_{90}$(non-agglomerated particles).

6. The method according to claim 1, wherein the method is carried out continuously by active ingredient solution and optionally antisolvent being fed continuously and active ingredient particles as well as liquid phase being continuously removed.

7. The method according to claim 1, wherein a power input of the ultrasound is in the range from 50 to 500 watts per liter suspension.

* * * * *